(12) United States Patent
Park et al.

(10) Patent No.: US 10,639,398 B2
(45) Date of Patent: May 5, 2020

(54) TISSUE MATRICES INCORPORATING MULTIPLE TISSUE TYPES

(71) Applicant: LifeCell Corporation, Branchburg, NJ (US)

(72) Inventors: Sangwook Park, Dunellen, NJ (US); Hui Xu, Plainsboro, NJ (US); Aaron Barere, Hoboken, NJ (US); Israel Jessop, Annandale, NJ (US); Mrinal Shah, Parsippany, NJ (US); Nathaniel Bachrach, Clifton, NJ (US)

(73) Assignee: LifeCell Corporation, Madison, NJ (US)

( * ) Notice: Subject to any disclaimer, the term of this patent is extended or adjusted under 35 U.S.C. 154(b) by 344 days.

(21) Appl. No.: 15/639,592

(22) Filed: Jun. 30, 2017

(65) Prior Publication Data

US 2018/0008745 A1 Jan. 11, 2018

Related U.S. Application Data

(60) Provisional application No. 62/358,347, filed on Jul. 5, 2016.

(51) Int. Cl.
*A61F 2/12* (2006.01)
*A61L 27/56* (2006.01)
(Continued)

(52) U.S. Cl.
CPC ............ *A61L 27/3645* (2013.01); *A61F 2/12* (2013.01); *A61L 27/362* (2013.01);
(Continued)

(58) Field of Classification Search
CPC .... A61F 2/12; A61F 2/10; A61F 2/105; A61F 2013/00157; A61F 2013/00527;
(Continued)

(56) References Cited

U.S. PATENT DOCUMENTS 4,373,519 A 2/1983 Errede et al.
4,703,108 A 10/1987 Silver et al.
(Continued)

FOREIGN PATENT DOCUMENTS

WO 1990/00060 A1 1/1990
WO 2002/40630 A2 5/2002
(Continued)

OTHER PUBLICATIONS

Badylak et al., Extracellular matrix as a biological scaffold material: Structure and function. Acta Biomater. Jan. 2009;5(1):1-13.
(Continued)

*Primary Examiner* — Dinah Baria
(74) *Attorney, Agent, or Firm* — McCarter & English, LLP

(57) ABSTRACT

The present disclosure provides tissue products produced from extracellular tissue matrices. The tissue products can include acellular extracellular matrices including combinations of different tissue types. The combination can harness various properties of the different tissues to provide improved composite structures with desired mechanical and/or biologic properties.

24 Claims, 10 Drawing Sheets

(51) Int. Cl.
*A61L 27/36* (2006.01)
*A61L 27/48* (2006.01)
*A61L 27/60* (2006.01)

(52) U.S. Cl.
CPC ....... *A61L 27/3604* (2013.01); *A61L 27/3633* (2013.01); *A61L 27/48* (2013.01); *A61L 27/56* (2013.01); *A61L 27/60* (2013.01)

(58) Field of Classification Search
CPC .... A61L 27/362; A61L 27/56; A61L 27/3645; A61L 27/3604; A61L 27/60
See application file for complete search history.

(56) References Cited

U.S. PATENT DOCUMENTS

| | | | |
|---|---|---|---|
| 4,950,483 | A | 8/1990 | Ksander et al. |
| 5,298,015 | A | 3/1994 | Komatsuzaki et al. |
| 5,336,616 | A | 8/1994 | Livesey et al. |
| 5,993,844 | A | 11/1999 | Abraham et al. |
| 6,166,288 | A | 12/2000 | Diamond et al. |
| 6,933,326 | B1 | 8/2005 | Griffey et al. |
| 7,070,584 | B2 | 7/2006 | Johnson et al. |
| 7,166,477 | B2 | 1/2007 | Prusiner et al. |
| 7,358,284 | B2 | 4/2008 | Griffey et al. |
| 7,700,819 | B2 | 4/2010 | Ambrosio et al. |
| 7,883,541 | B2 | 2/2011 | Mills et al. |
| 8,110,216 | B2 | 2/2012 | Ambrosio et al. |
| 8,197,551 | B2 | 6/2012 | Swain et al. |
| 8,267,918 | B2 | 9/2012 | Johnson et al. |
| 8,333,803 | B2 | 12/2012 | Park et al. |
| 8,460,691 | B2 * | 6/2013 | Lauritzen ............... A61K 38/39 424/422 |
| 8,735,054 | B1 | 5/2014 | Sun et al. |
| 8,741,354 | B2 * | 6/2014 | Johnson ................. A61L 27/56 424/550 |
| 9,339,369 | B2 | 5/2016 | McQuillan et al. |
| 9,382,422 | B2 | 7/2016 | Owens et al. |
| 9,421,306 | B2 | 8/2016 | Park et al. |
| 2002/0128724 | A1 | 9/2002 | Ollerenshaw et al. |
| 2002/0193448 | A1 | 12/2002 | Wallace et al. |
| 2003/0035843 | A1 | 2/2003 | Livesey et al. |
| 2003/0143207 | A1 | 7/2003 | Livesey et al. |
| 2005/0028228 | A1 | 2/2005 | McQuillan et al. |
| 2005/0043819 | A1 | 2/2005 | Schmidt et al. |
| 2006/0153816 | A1 | 7/2006 | Brown et al. |
| 2006/0210960 | A1 | 9/2006 | Livesey et al. |
| 2008/0027562 | A1 | 1/2008 | Fujisato et al. |
| 2008/0114277 | A1 | 5/2008 | Ambrosio et al. |
| 2009/0035289 | A1 | 2/2009 | Wagner et al. |
| 2009/0130221 | A1 | 5/2009 | Bolland et al. |
| 2009/0157017 | A1 | 6/2009 | Ambrosio |
| 2009/0220579 | A1 | 9/2009 | Hassingboe et al. |
| 2009/0287181 | A1 | 11/2009 | Kagan |
| 2009/0306790 | A1 | 12/2009 | Sun |
| 2010/0040687 | A1 | 2/2010 | Pedrozo et al. |
| 2010/0179515 | A1 | 7/2010 | Swain et al. |
| 2010/0233235 | A1 | 9/2010 | Matheny et al. |
| 2011/0021753 | A1 | 1/2011 | Huang |
| 2011/0054588 | A1 | 3/2011 | Xu et al. |
| 2011/0251566 | A1 | 10/2011 | Zimnitsky et al. |
| 2012/0010728 | A1 | 1/2012 | Sun et al. |
| 2012/0276213 | A1 | 11/2012 | Chen |
| 2012/0310367 | A1 | 12/2012 | Connor |
| 2014/0004549 | A1 | 1/2014 | Chen et al. |
| 2014/0088701 | A1 | 3/2014 | Sun et al. |
| 2014/0377833 | A1 | 12/2014 | Chen et al. |
| 2015/0282925 | A1 | 10/2015 | Xu et al. |
| 2016/0228235 | A1 | 8/2016 | McQuillan et al. |
| 2016/0317707 | A1 | 11/2016 | Owens et al. |
| 2016/0317711 | A1 | 11/2016 | Park et al. |
| 2017/0021058 | A1 * | 1/2017 | Huang ................. A61L 27/3604 |
| 2017/0224869 | A1 | 8/2017 | Shah et al. |

FOREIGN PATENT DOCUMENTS

| | | | | |
|---|---|---|---|---|
| WO | 2011/019822 A2 | 2/2011 | | |
| WO | WO-2014008181 A2 * | 1/2014 | ............. | A61K 35/34 |

OTHER PUBLICATIONS

Bellows et al., Abdominal wall repair using human acellular dermis. Am J Surg. Aug. 2007;194(2):192-8.

Blackburn et al., Negative-pressure dressings as a bolster for skin grafts. Ann Plast Surg. May 1998;40(5):453-7.

Brandi et al., Treatment with vacuum-assisted closure and cryopreserved homologous de-epidermalised dermis of complex traumas to the lower limbs with loss of substance, and bones and tendons exposure. J Plast Reconstr Aesthet Surg. Dec. 2008;61(12):1507-11.

Choi et al., Decellularized extracellular matrix derived from human adipose tissue as a potential scaffold for allograft tissue engineering. J Biomed Mater Res A. Jun. 1, 2011;97(3):292-9.

Choi et al., Fabrication of porous extracellular matrix scaffolds from human adipose tissue. Tissue Eng Part C Methods. Jun. 2010;16(3):387-96.

Collins et al., Cardiac xenografts between primate species provide evidence for the importance of the alpha-galactosyl determinant in hyperacute rejection. J Immunol. May 15, 1995;154(10):5500-10.

Crapo et al., An overview of tissue and whole organ decellularization processes. Biomaterials. Apr. 2011;32(12):3233-43.

Dagalakis et al., Design of an artificial skin. Part III. Control of pore structure. J Biomed Mater Res. Jul. 1980;14(4):511-28.

Dattilo et al., Medical Textiles: Application of an Absorbable Barbed Bi-directional Surgical Suture. Journal of Textile and Apparel, Technology and Management. 2002;2(2):1-5.

DeQuach et al., Injectable skeletal muscle matrix hydrogel promotes neovascularization and muscle cell infiltration in a hindlimb ischemia model. Eur Cell Mater. Jun. 5, 2012;23:400-12; discussion 412.

Dobrin et al., Elastase, collagenase, and the biaxial elastic properties of dog carotid artery. Am J Physiol. Jul. 1984;247(1 Pt 2):H124-31.

Galili et al., Interaction between human natural anti-alphagalactosyl immunoglobulin G and bacteria of the human flora. Infect Immun. Jul. 1988;56(7):1730-7.

Galili et al., Man, apes, and Old World monkeys differ from other mammals in the expression of alpha-galactosyl epitopes on nucleated cells. J Biol Chem. Nov. 25, 1988;263(33)17755-62.

Galili, Interaction of the natural anti-Gal antibody with alphagalactosyl epitopes: a major obstacle for xenotransplantation in humans. Immunol Today. Oct. 1993;14(10):480-2.

Good et al., Identification of carbohydrate structures that bind human antiporcine antibodies: implications for discordant xenografting in humans. Transplant Proc. Apr. 1992;24(2):559-62.

Griffey et al., Particulate dermal matrix as an injectable soft tissue replacement material. J Biomed Mater Res. 2001;58(1):10-5.

Hamadeh et al., Human natural anti-Gal IgG regulates alternative complement pathway activation on bacterial surfaces. J Clin Invest. Apr. 1992;89(4):1223-35.

Ionescu et al., Effect of Papain and Bromelin on Muscle and Collagen Proteins in Beef Meal the Annals of the University Dunarea de Jos of Galati, Fascicle VI—Food Technology, New Series Year II (XXXI). pp. 9-16 (2008).

Ju et al., Beneficial effect of hydrophilized porous polymer scaffolds in tissue-engineered cartilage formation. J Biomed Mater Res B Appl Biomater. Apr. 2008;85(1):252-60.

Karlinsky et al., In vitro effects of elastase and collagenase on mechanical properties of hamster lungs. Chest. Feb. 1976;69(2 Suppl):275-6.

Lu et al., Novel porous aortic elastin and collagen scaffolds for tissue engineering. Biomaterials. Oct. 2004;25(22):5227-37.

Merritt et al., Functional assessment of skeletal muscle regeneration utilizing homologous extracellular matrix as scaffolding. Tissue Eng Part A. Apr. 2010;16(4):1395-405.

O'Brien et al., The effect of pore size on cell adhesion in collagen-GAG scaffolds. Biomaterials. Feb. 2005;26(4):433-41.

(56) References Cited

OTHER PUBLICATIONS

Randall et al., Use of an acellular regenerative tissue matrix in combination with vacuum-assisted closure therapy for treatment of a diabetic foot wound. J Foot Ankle Surg. Sep.-Oct. 2008;47(5):430-3.
Reihsner et al., Biomechanical properties of elastase treated palmar aponeuroses. Connect Tissue Res. 1991;26(1-2):77-86.
Sandrin et al., Anti-pig IgM antibodies in human serum react predominantly with Gal(alpha 1-3)Gal epitopes. Proc Natl Acad Sci U S A. Dec. 1, 1993;90(23):11391-5.
Stern et al., The influence of extracellular matrix derived from skeletal muscle tissue on the proliferation and differentiation of myogenic progenitor cells ex vivo. Biomaterials. Apr. 2009;30(12):2393-9.
Tedder et al., Stabilized collagen scaffolds for heart valve tissue engineering. Tissue Eng Part A. Prepublication, 12 pages, DOI: 10.1089/ten.tea.2008.0263. (2008).
Turner et al., Regeneration of skeletal muscle. Cell Tissue Res. Mar. 2012;347(3):759-74.
Valentin et al., Functional skeletal muscle formation with a biologic scaffold. Biomaterials. Oct. 2010;31(29):7475-84.
Wei et al., Construction of varying porous structures in acellular bovine pericardia as a tissue-engineering extracellular matrix. Biomaterials. May 2005;26(14):1905-13.
Wolf et al., Biologic scaffold composed of skeletal muscle extracellular matrix. Biomaterials. Apr. 2012;33(10):2916-25.
Wu et al., An injectable adipose matrix for soft-tissue reconstruction. Plastic and Reconstructive Surgery Advance Online Article. 33 pages. DOI: 10.1097/PRS.0b013e31824ec3dc. (2011).
Wu et al., Preparation of collagen-based materials for wound dressing. Chin Med J (Engl). Mar. 2003;116(3):419-23.
Xu et al., A porcine-derived acellular dermal scaffold that supports soft tissue regeneration: removal of terminal galactose-alpha-(1,3)-galactose and retention of matrix structure. Tissue Eng Part A. Prepublication. 13 pages. DOI: 10.1089/ten.tea.2008.0384. (2009).
Yang et al., A cartilage ECM-derived 3-D porous acellular matrix scaffold for in vivo cartilage tissue engineering with PKH26-labeled chondrogenic bone marrow-derived mesenchymal stem cells. Biomaterials. May 2008;29(15):2378-87.
Yuan et al., Effects of collagenase and elastase on the mechanical properties of lung tissue strips. J Appl Physiol (1985). Jul. 2000;89(1):3-14.
U.S. Appl. No. 14/255,559 Specification. Methods for Making Acellular Tissue Matrices. Filed Apr. 17, 2014. 98 pages.
International Search Report and Written Opinion for Application No. PCT/US2017/040190, dated Oct. 11, 2017. 13 pages.

\* cited by examiner

TISSUE MATRICES INCORPORATING MULTIPLE TISSUE TYPES

This application claims priority under 35 USC § 119 to U.S. Provisional Application No. 62/358,347, which was filed on Jul. 5, 2016 and is herein incorporated by reference in its entirety.

BACKGROUND

The present disclosure relates to tissue products, and more particularly, to tissue matrices produced from a combination of two or more different tissue types.

Various tissue matrix products (e.g., acellular tissue matrices or similar tissue-derived or tissue regenerative materials) are currently available. Such products can be used to regenerate, reinforce, replace, and/or augment existing tissues, or tissues damaged or lost due to disease, trauma, surgery, radiation, or other events. Such materials can be very effective for treatment of many conditions. For example, acellular tissue matrix products such as ALLODERM®, an acellular human dermal matrix, and STRATTICE™, an acellular porcine dermal matrix (both from LIFECELL® CORPORATION, BRANCHBURG, N.J.), are useful for many surgical procedures, including abdominal wall defect repair and breast reconstruction.

Although currently available acellular tissue matrix products can be very effective at regenerating a range of tissue types, there remains a need for tissue matrix products that harness the beneficial regenerative and structural properties of tissue products derived from multiple tissue types. Accordingly, the present disclosure provides improved tissue matrix products that include combinations of two or more tissue matrix materials (i.e., materials derived from two or more types of tissues). The tissue matrix materials are arranged to provide improved methods of treatment—in some case, taking advantage of the biologic and mechanical properties of each of the component materials.

According to one embodiment, a tissue product is provided. The product can include a first component comprising an intact acellular tissue matrix and a second component comprising a porous acellular tissue matrix sponge covering at least a portion of the intact acellular tissue matrix. The porous acellular tissue matrix sponge comprises a tissue matrix that has been mechanically homogenized, resuspended, and stabilized, and wherein the intact acellular tissue matrix and porous acellular tissue matrix sponge are attached such that the intact acellular tissue matrix provides mechanical support to the porous acellular tissue matrix sponge.

According to one embodiment, a tissue product is provided. The product can include a first component comprising a sheet of acellular tissue matrix, and a second component comprising a porous acellular tissue matrix sponge covering at least a portion of the intact acellular tissue matrix. The second component may consist essentially of adipose tissue matrix.

According to one embodiment, a tissue product is provided. The tissue product can include a first component comprising a sheet of acellular tissue matrix and a second component comprising a sheet of a second acellular tissue matrix derived from a tissue type different than that of the first component. The product can further comprise a third component including a porous acellular tissue matrix sponge, wherein the third component is contained between the first component and the second component.

DESCRIPTION OF CERTAIN EXEMPLARY EMBODIMENTS

Figure 1A:
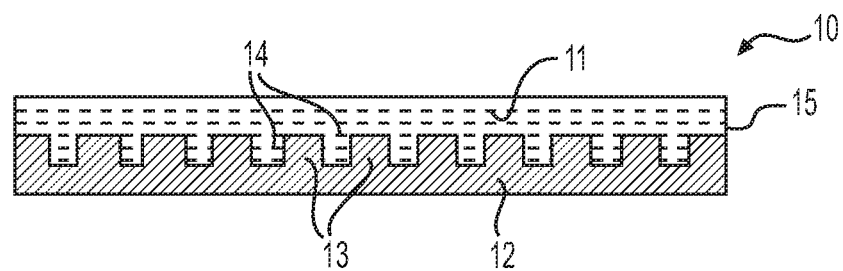
FIG. 1A is a side cut away view of a tissue product including tissue matrix from two or more tissue types, according to various embodiments.

Reference will now be made in detail to certain exemplary embodiments according to the present disclosure, certain examples of which are illustrated in the accompanying drawings. Wherever possible, the same reference numbers will be used throughout the drawings to refer to the same or like parts.

In this disclosure, the use of the singular includes the plural unless specifically stated otherwise. In this disclosure, the use of "or" means "and/or" unless stated otherwise. Furthermore, the use of the term "including", as well as other forms, such as "includes" and "included", is not limiting. Any range described herein will be understood to include the endpoints and all values between the endpoints.

The section headings used herein are for organizational purposes only and are not to be construed as limiting the subject matter described. All documents, or portions of documents, cited in this disclosure, including but not limited to patents, patent applications, articles, books, and treatises, are hereby expressly incorporated by reference in their entirety for any purpose.

Various human and animal tissues can be used to produce products for treating patients. For example, various tissue products for regeneration, repair, augmentation, reinforcement, and/or treatment of human tissues that have been damaged or lost due to various diseases and/or structural damage (e.g., from trauma, surgery, atrophy, and/or long-term wear and degeneration) have been produced. Such products can include, for example, acellular tissue matrices, tissue allografts or xenografts, and/or reconstituted tissues (i.e., at least partially decellularized tissues that have been seeded with cells to produce viable materials).

A variety of tissue products have been produced for treating soft and hard tissues. For example, ALLODERM® and STRATTICE™ (LIFECELL CORPORATION, Branchburg, N.J.) are two dermal acellular tissue matrices made from human and porcine dermis, respectively. Although such materials are very useful for treating certain types of conditions, materials having different biological and/or mechanical properties may be desirable for certain applications. For example, ALLODERM® and STRATTICE™ have been used to assist in treatment of structural defects and/or to provide support to tissues (e.g., for abdominal walls or in breast reconstruction), and their strength and biological properties make them well-suited for such uses.

Such materials, however, may not be ideal for regeneration, repair, replacement, and/or augmentation of certain soft-tissue defects. For example, improved tissue fillers for replacing lost or damaged tissues, including adipose or other soft tissues in the form of porous sponges, may be beneficial for some patients. Such porous sponges, however, may lack sufficient structural integrity for certain uses.

For example, tissue matrix sponges may have insufficient tensile strength, burst strength, or suture retention strength to provide needed support in various procedures such as breast reconstruction, breast augmentation, abdominal wall defect treatment, or treatment of soft tissues that are subjected to repeated movements, or even occasionally experience relatively high mechanical stresses. In addition, some materials may have less than optimal compressive elasticity and strength, bending rigidity, kink resistance, or abrasion resistance. Accordingly, improved devices and methods are provided herein.

The improved devices incorporate combinations of tissue matrix sponges (e.g., adipose tissue matrix sponges) along with intact acellular tissue matrices, such as dermal, facial, or muscle tissue matrices. The improved devices are joined to harness properties of the different tissue matrices, thereby providing improved regenerative biologic and mechanic properties for certain uses.

As used herein, the term "intact acellular tissue matrix" refers to an extracellular tissue matrix having a shape and form substantially similar to the tissue from which the matrix is derived, although it will be understood that production of the acellular matrix (e.g., by removing cells) will produce a matrix that is modified from the original tissue matrix, by for example, changing the microstructure of the matrix. For example, an "intact acellular tissue matrix" produced from elongated, sheet-like tissue such as dermis, bladder, intestinal layer(s), stomach layer(s), dura, pericardium, or fascia may be in the form of a sheet formed by the original protein structure. Such "intact acellular tissue matrices", however, can include openings, meshes, or holes, as discussed further below, and may be modified, e.g., by cross-linking, enzymatic treatment, or chemical modification. "Intact acellular tissue matrices" would not include tissues that have been ground, cut, homogenized, or otherwise processed to form small tissue fragments or particles, even if such fragments or particles are resuspended or otherwise processed to produce a sheet or other form.

Accordingly, in various embodiments, tissue products for treatment or regeneration of tissue are provided. The tissue products can include a first component comprising an intact acellular tissue matrix and a second component comprising a porous acellular tissue matrix sponge. The porous acellular tissue matrix may cover at least a portion of the intact acellular tissue matrix, or alternatively or additionally, the porous acellular tissue matrix can be positioned near the intact acellular tissue matrix during a surgical procedure. The porous acellular tissue matrix sponge can be produced in a variety of ways, as discussed further below.

FIGS. 1A-11 illustrate tissue products or methods of using the tissue products of the present disclosure in different embodiments and configurations. FIGS. 1A-1D illustrate side cut away views of various tissue products, and FIGS. 2A-2B are perspective views of the devices of FIGS. 1B and 1C, respectively.

As shown, the products of FIGS. 1A-1D (10, 20, 30, 40) can include multiple components. As discussed above, the products can include a first component (12, 22, 32, 42) and a second component (11, 21, 31, 41). The first component (12, 22, 32, 42) can include an intact acellular tissue matrix, and the second component (11, 21, 31, 41) can include a porous tissue matrix sponge, both of which will be described in more detail.

The first component (12, 22, 32, 42) can include a variety of suitable acellular tissue matrices in the form of a sheet, or other suitable three-dimensional structure, including for example, folded shapes, boxes, cup-like shapes, tubes, irregular or repeating patterned shapes, spheres or other rounded 3-D shapes. The intact tissue matrix (first component) can be formed from a variety of different tissue sources and can be processed and configured to provide structure support or mechanical stability to the devices (10, 20, 30, 40).

The tissue matrices used to produce the first component (12, 22, 32, 42) can include a variety of suitable tissue matrix materials. Examples of the tissues that may be used to construct the tissue matrices for the first component can include, but are not limited to, skin, parts of skin (e.g., dermis), fascia, muscle (striated, smooth, or cardiac), pericardial tissue, dura, umbilical cord tissue, placental tissue, cardiac valve tissue, ligament tissue, tendon tissue, blood vessel tissue, such as arterial and venous tissue, cartilage, bone, neural connective tissue, urinary bladder tissue, ureter tissue, and intestinal tissue. For example, a number of biological scaffold materials that may be used for the first component are described by Badylak et al., Badylak et al., "Extracellular Matrix as a Biological Scaffold Material: Structure and Function," *Acta Biomaterialia* (2008), doi: 10.1016/j.actbio.2008.09.013. In some cases, the first component includes a sheet of acellular tissue matrix derived from human or porcine dermis. Suitable human and porcine dermal materials include, for example, ALLODERM® and STRATTICE™, respectively.

The first component (12, 22, 32, 42) can be selected based on both biologic and mechanical properties. For example, suitable tissue matrix materials used to produce the first component will generally be capable of providing a regenerative tissue scaffold suitable for supporting the ingrowth of native cells and formation of tissue without excessive inflammation and with minimal scar formation.

In addition, the first component (12, 22, 32, 42) can be selected based on its ability to provide a desired amount of structural support. For example, the first component (12, 22, 32, 42) may possess sufficient tensile strength, burst strength, and suture retention strength to allow use of the device for treatment of such conditions as complex or simple abdominal wall defects, defects associated with surgical oncology for treatment of breast cancer, treatment of structural defects in connective tissues (e.g., fascia, tendons, or ligaments), and/or to provide structural support around breast implants or tissue expanders used in augmentation or reconstruction.

As noted above, however, the devices can include a second component (11, 21, 31, 41), and the second component can be selected to provide specific biologic and mechanical properties. For example, in one embodiment, the second component includes a tissue matrix derived from adipose tissue. The tissue matrix derived from adipose tissue can be selected based on its ability to support regeneration of certain tissue types, including regeneration of adipose tissue, or predominantly adipose tissue; and may be selected to produce a desired feel, compressibility, size, shape, or other mechanical features. As such, the second component can support a desired level of adipose regeneration, which may be desirable for various anatomic sites, including, for example, the breast (e.g., after surgical removal of tumors or for augmentation), the buttocks, thighs, neck, face, or any other site where adipose tissue may be desirable to produce a certain feel, cosmetic appearance, biologic property, or other intended result.

The first component (12, 22, 32, 42) and second component (11, 21, 31, 41) can be arranged in a variety of ways to produce desired mechanical and biologic properties when implanted in vivo. For example, FIGS. 1A-1D illustrate various configurations of devices (10, 20, 30, 40) consistent with the present invention.

As shown in FIG. 1A, the first component 12 can be formed as a sheet of intact acellular tissue (e.g., acellular dermal matrix), and the second component 11 can be formed on one side of the first component 12 to produce a bilayer sheet or composite structure (e.g., having a sheet of the first component 12 with a mass of the second component 11 as a sheet or other configuration). In one embodiment, the device 10 can optionally include a textured surface 15 on at least one side of the sheet of first component 12 to assist in mechanical attachment of the first component 12 and second component 11.

Figure 1B:
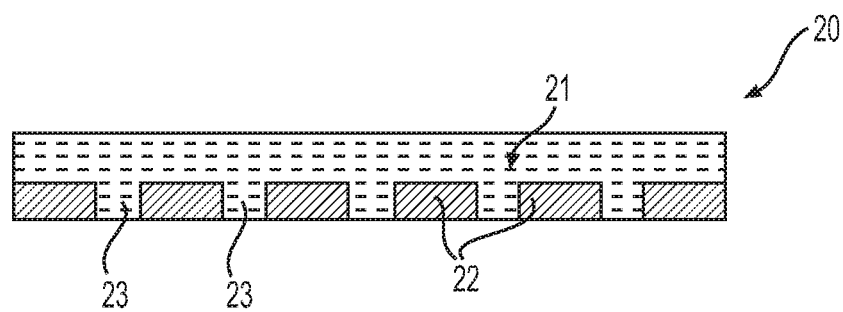
FIG. 1B is a side cut away view of a tissue product including tissue matrix from two or more tissue types, according to various embodiments.
Figure 1C:
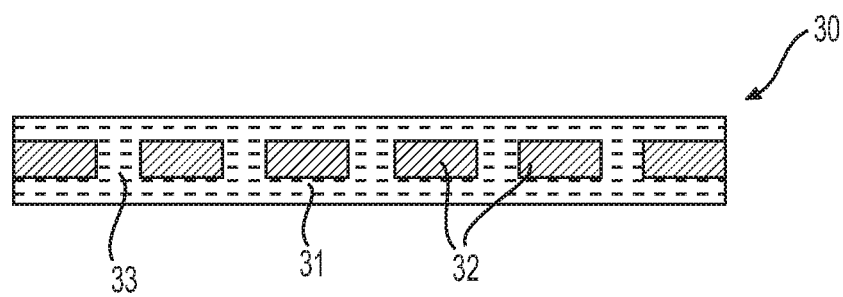
FIG. 1C is a side cut away view of a tissue product including tissue matrix from two or more tissue types, according to various embodiments.
Figure 1D:
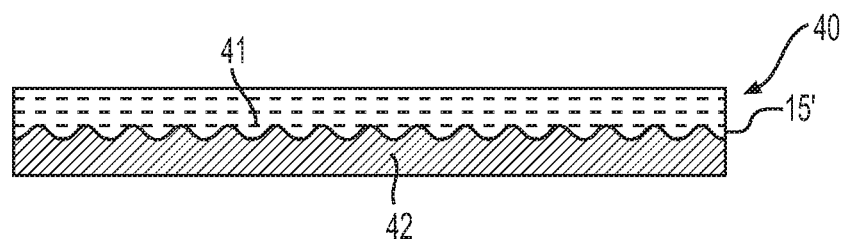
FIG. 1D is a side cut away view of a tissue product including tissue matrix from two or more tissue types, according to various embodiments.
Figure 2A:
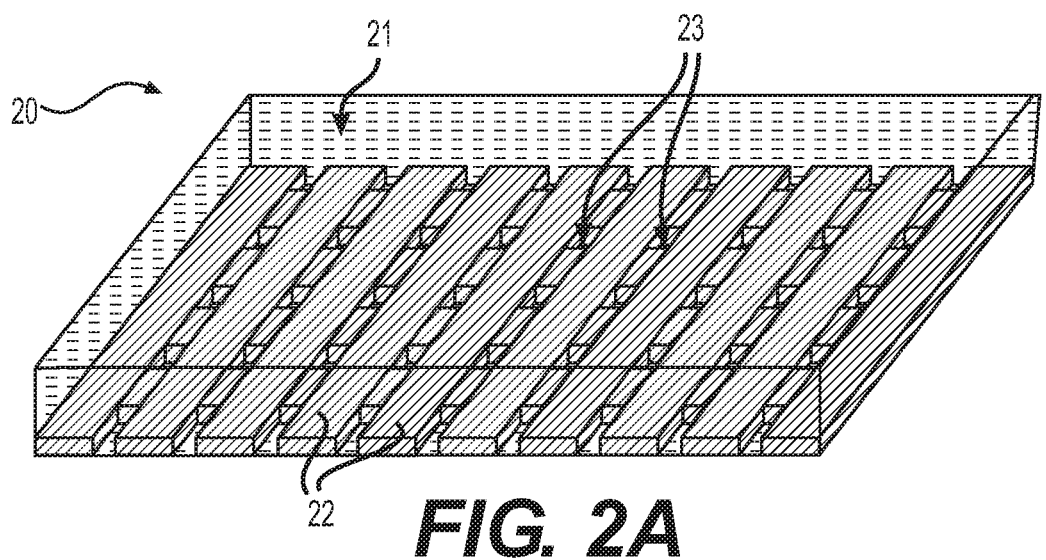
FIG. 2A is a perspective view of the tissue product of FIG. 1B.
Figure 2B:
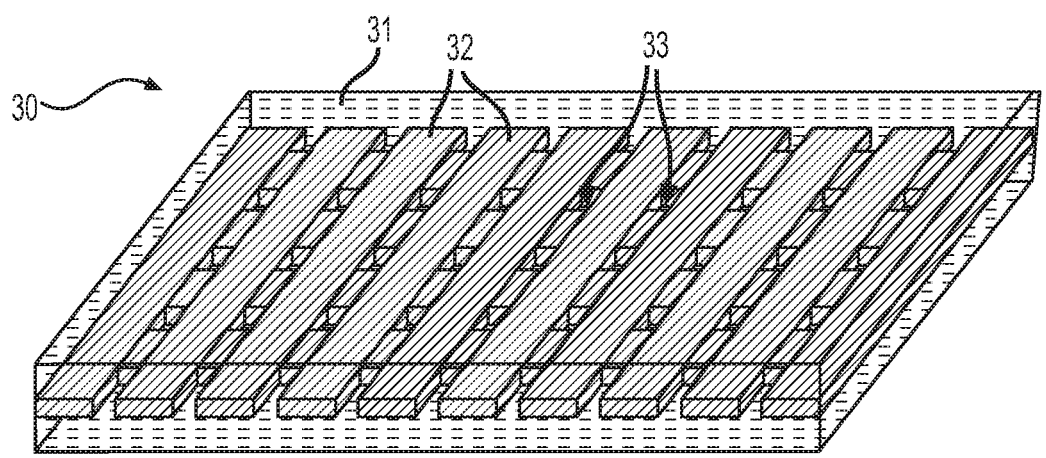
FIG. 2B is a perspective view of the tissue product of FIG. 1C.

The textured surface 15 can facilitate joining between the first component 12 and the tissue fibers in a slurry or suspension used for form the second component 11 (discussed below). The textures can be grooves or holes, or can include a roughened surface such that it creates jagged edges or textures with some loose collagen fibers that facilitate cross-linking. The textured surface 15 can include a surface roughening (e.g., formed by scraping or other mechanical process). In addition, the textured surface 15 can include indentations 14 and/or protrusions 13 that allow interdigitaion of the first and second components. Alternatively, as shown in FIG. 1D, the textured surface 15' can include small irregularities or changes in the surface shape for the first component 42 and or second component 41.

Furthermore, although the embodiments described above with respect to FIGS. 1A, 1B, and 1D illustrate a device having the second component attached to or covering one side of a sheet of the first component, it will be appreciated that the second component may be applied to both sides (e.g., the top and bottom) of a sheet of the first component, or may be applied only to a portion of one or both of the top and bottom surfaces of the first component.

In other embodiments, the first component can be in the form of a sheet having openings or a mesh structure in which the second component can be positioned. For example, FIGS. 1B and 1C illustrate devices 20, 30 having a first component 22, 32 in the form of a sheet with openings 23, 33, and including a second component 21, 31 covering one or both sides of the sheet of first component 22, 32, while filing the openings 22, 32. Such configurations are illustrated in more detail in FIGS. 2A and 2B, which provide perspective views of the devices of FIGS. 1B and 1C, respectively.

Figure 4:
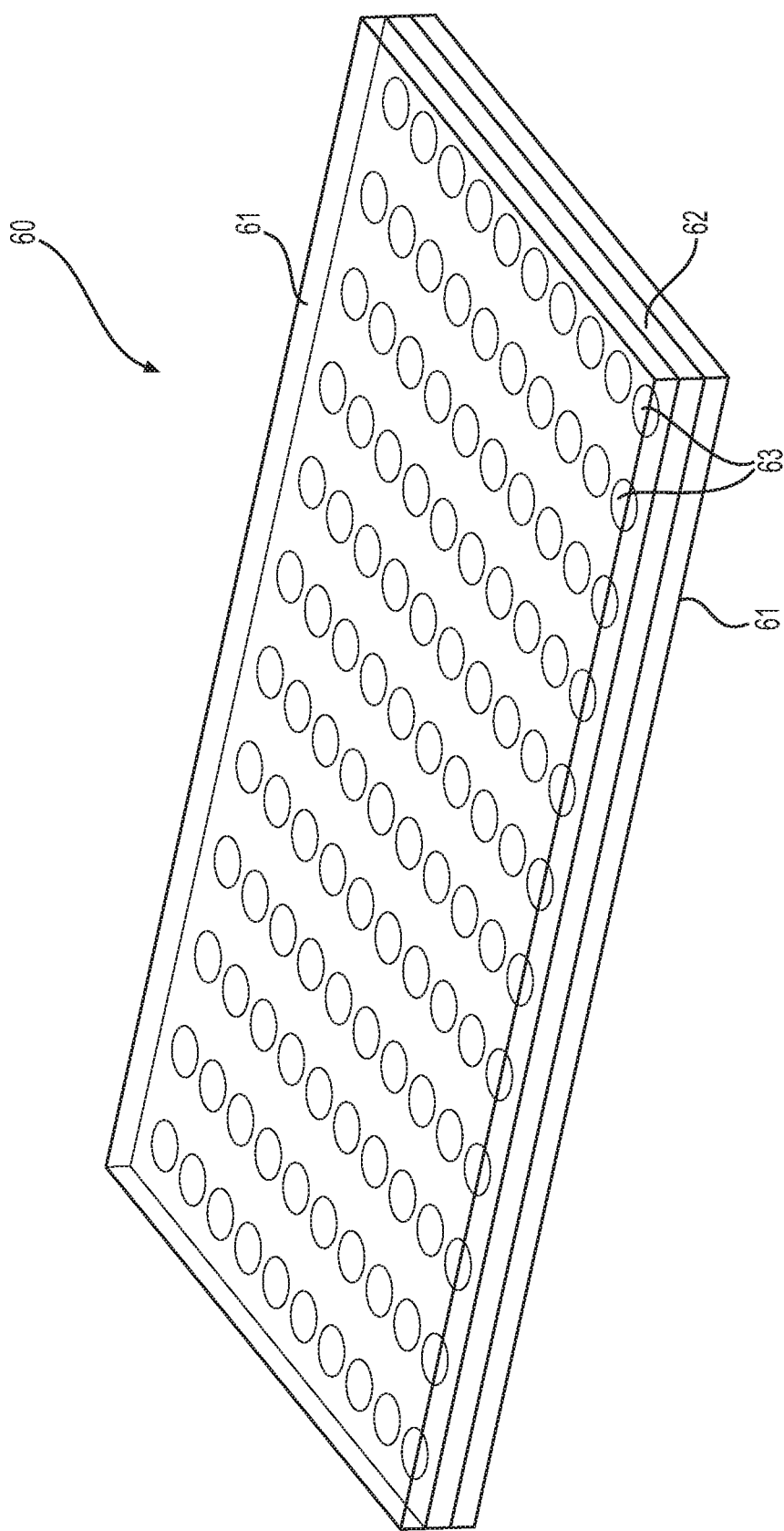
FIG. 4 is a perspective view of another tissue product including a sheet of acellular tissue matrix and a porous tissue matrix sponge covering opposing sides of the tissue matrix.
Figure 5:
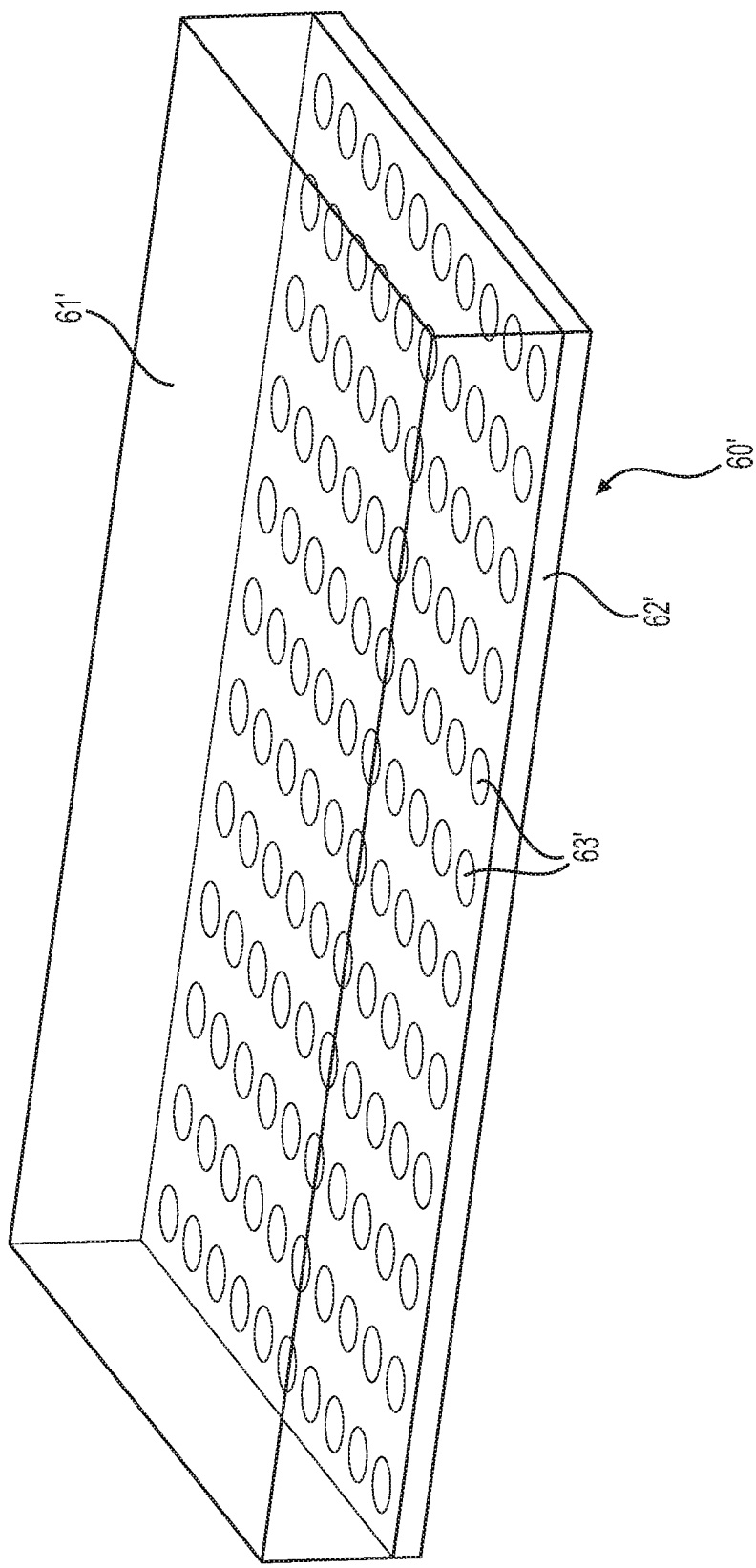
FIG. 5 is a perspective view of another tissue product including a sheet of acellular tissue matrix and a porous tissue matrix sponge covering a side of the tissue matrix.

It should be noted, that the pattern of openings or meshwork in the devices of FIGS. 1A and 1B can be varied based on a number of factors. For example, FIGS. 4 and 5 are perspective views of tissue products including a sheet acellular tissue matrix and a porous tissue matrix sponge covering one side or both opposing sides of the tissue matrix. As shown, FIG. 4 illustrates a device 60 including a sheet of the first component (an intact acellular tissue matrix) 62 with openings 63 formed as circular holes. In addition, the device 60 includes a second component 61 covering an opposing side of the sheet of the first component 62 and filling the openings 63. Similarly, the device 60' of FIG. 5 includes a sheet of the first component (an intact acellular tissue matrix) 62' with openings 63' formed as circular holes. In addition, the device 60' includes a second component 61' covering one side of the sheet of the first component 62' and filling the openings 63'.

The devices illustrated in FIGS. 4-5 (as well as those in FIGS. 1A-2B) can be used for breast reconstruction applications or other treatments. The size of the openings 63 can be selected based on the desired strength, wherein the size of the openings 63 and spacing of openings can be varied to produce desired properties. The size and number of the openings can be selected to modulate the rate of cellular ingrowth into the openings 63 (or corresponding parts of FIGS. 1A-2B). In addition, the second component 61 can be formed of a material that is more suitable for cellular ingrowth, and may provide a better biological response while harnessing the mechanical properties of the first component 62.

The devices illustrated in FIGS. 4-5 (as well as those in FIGS. 1A-2B) can be designed for specific applications. The designs may depend on the specifics of the application. For example, the design in an application where strength needs to be maintained, shear is low, and fluid flow across the intact matrix is not important (e.g., facial reconstruction or minimally invasive facelifts) can include smaller openings 63. Conversely, when more compressibility is important, larger and more openings 63 might be better.

Figure 3:
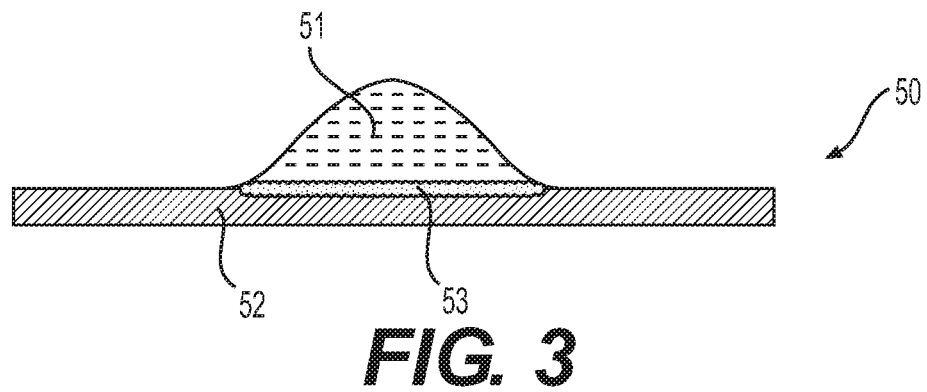
FIG. 3 is a side cut away view of a tissue product including tissue matrix from two or more tissue types, according to various embodiments.

In some embodiments, the second component may cover or be applied to only a portion of a surface of the first component, and/or may be applied as a bulk material having a desired shape. For example, FIG. 3 is a side cut away view of another tissue product, according to various embodiments. As shown the device 50 of FIG. 3 includes a sheet of the first component 52, with the second component 51 covering a limited section 53 of the first component, but it should be understood that the second component may cover more or different sections. The section 53 may have a modified surface (e.g., by roughening or texturing) that facilitates stronger bonding between the second component 51. As such, the second component can be in the form of a bulky or larger mass, and the device 50 may be used, for example, in breast surgery, wherein the first component 52 provides structural support, e.g., to attach to the chest wall or muscle, and the second component 51 provides an improved biological response to allow rapid ingrowth to produce tissue with a desired composition, texture, feel, and biological properties.

Figure 11:
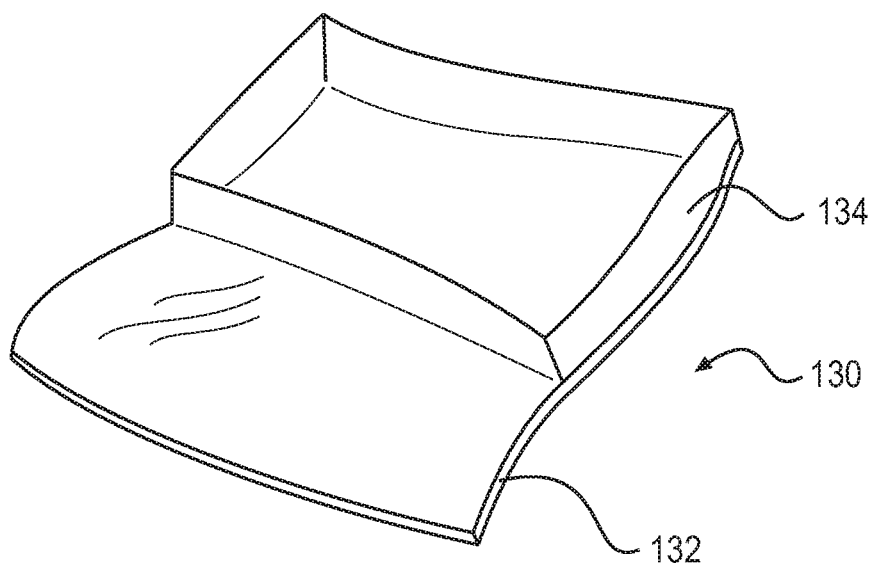
FIG. 11 is a perspective view of another tissue product including a sheet of acellular tissue matrix and a porous tissue matrix sponge.

Similar to the device of FIG. 3, FIG. 11 is a perspective view of another tissue product 130 including a sheet 132 of intact acellular tissue matrix and a porous tissue matrix sponge 134. FIG. 11 is intended to illustrate that the sponge 134 (corresponding to the second component 51 of FIG. 3) can include a variety of configurations (e.g., covering differing amounts of the sheet 132). The product 130 can, like the product of FIG. 3, be implanted to treat a breast, but as with FIG. 3's embodiment, could also be used to treat other sites (e.g., a facial defect, buttock, abdominal wall, or other structure). Furthermore, the components of the product 130 can be provided as a single device or as separate components to facilitate methods of treatment discussed further below.

The devices and methods described herein can also include more than two types of tissue matrices. Specifically, in some cases, the devices include a first component comprising a sheet of acellular tissue matrix and a second component comprising a sheet of a second acellular tissue matrix derived from a tissue type different than that of the first component. In addition, the devices can include a third component comprising a porous acellular tissue matrix sponge, wherein the third component is contained between the first component and the second component. Embodiments including such structures as well as their uses and methods of use are discussed further below.

Figure 6:
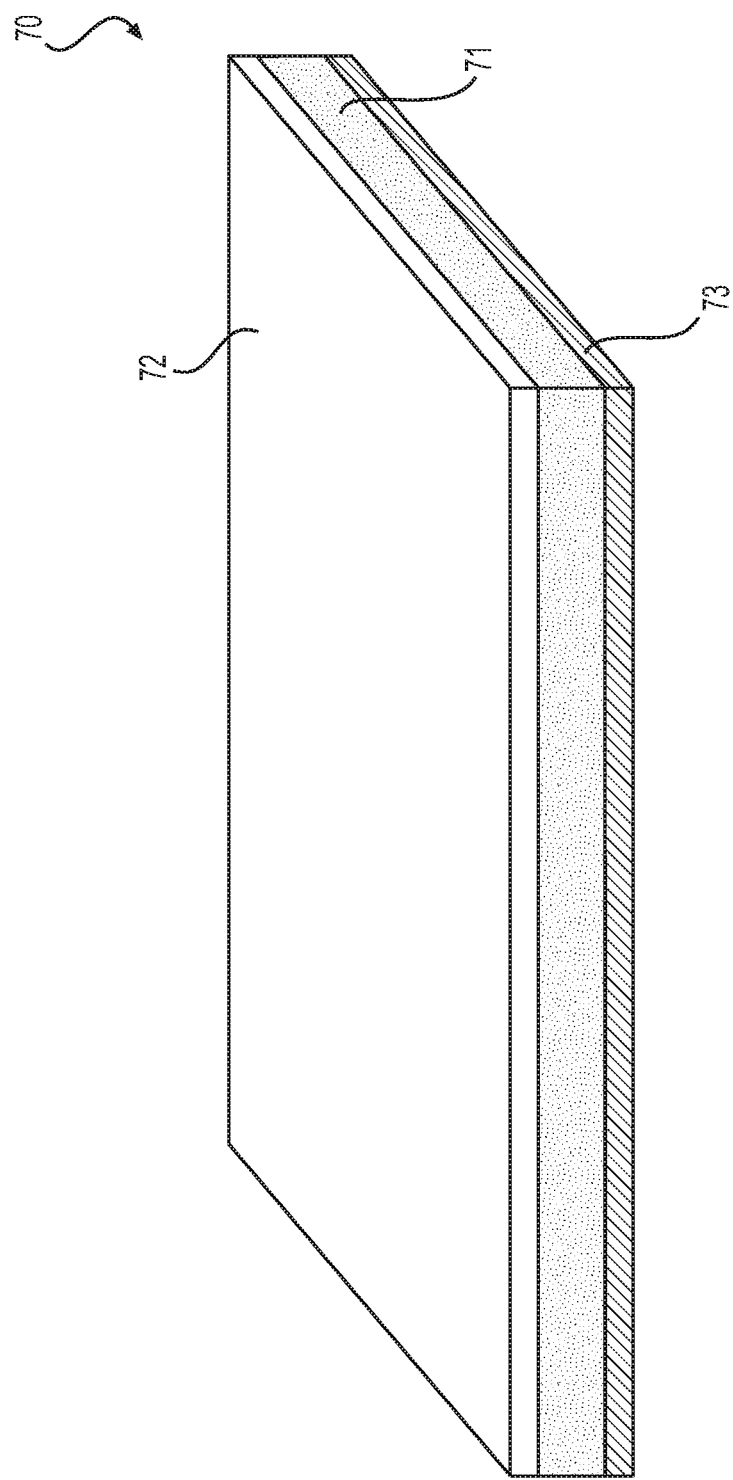
FIG. 6 is a perspective view of another tissue product including two sheets of acellular tissue matrix and a porous tissue matrix sponge secured between the sheets.

FIG. 6 is a perspective view of another tissue product 70 including two sheets 72, 73 of acellular tissue matrix and a porous tissue matrix sponge 71 secured between the sheets 72, 73. As shown, the device 70 is provided in the form of flat or flexible sheet of material, but may include a variety of different shapes, including a box-like shape. Alternatively, the device 70 can include any suitable three-dimensional form such as a spherical, ovoid, or irregular three-dimensional form.

Figure 9:
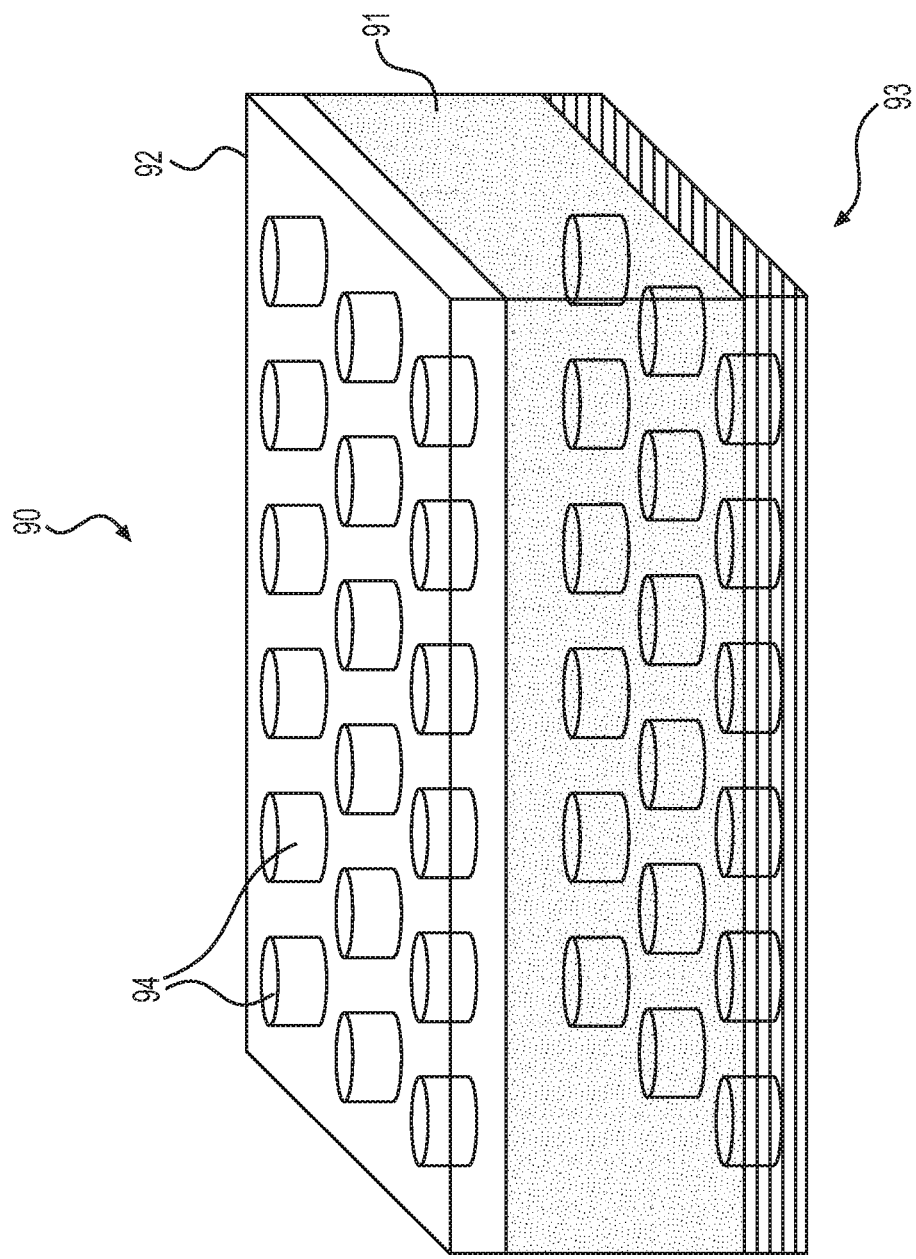
FIG. 9 is a perspective view of another tissue product including two sheets of acellular tissue matrix and a porous tissue matrix sponge secured between the sheets.

Furthermore, the configuration of FIG. 6 can be modified to include openings in the sheets 72, 73. For example, FIG. 9 illustrates an embodiment of a device 90, including sheets 92, 93, similar to those of FIG. 6, as well as a sponge 91, but further includes openings or perforations. The openings or perforations may include a variety of sizes, shapes, spacings, or configurations, as discussed above with respect to FIGS. 4 and 5.

In some cases, the device 70 of FIG. 6 can be modified to produce a material shaped for a specific use, e.g., as a breast implant. Suitable breast implants may be used, for example, for augmentation or reconstruction after procedures such as mastectomy, skin-sparing mastectomy, lumpectomy, or any other procedure such as revision breast augmentation, breast augmentation, or mastopexy.

Figure 7:
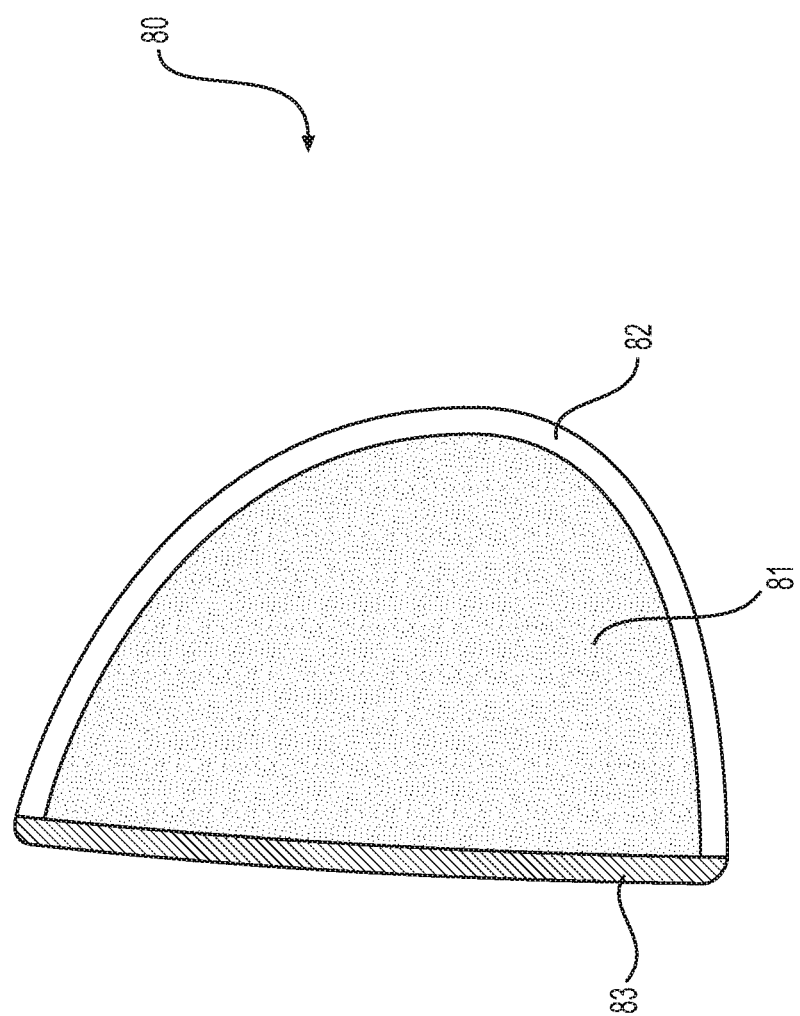
FIG. 7 is a side cut away view of another tissue product including two sheets of acellular tissue matrix and a porous tissue matrix sponge secured between the sheets, the tissue product forming a volume shaped for implantation within a breast.
Figure 8:
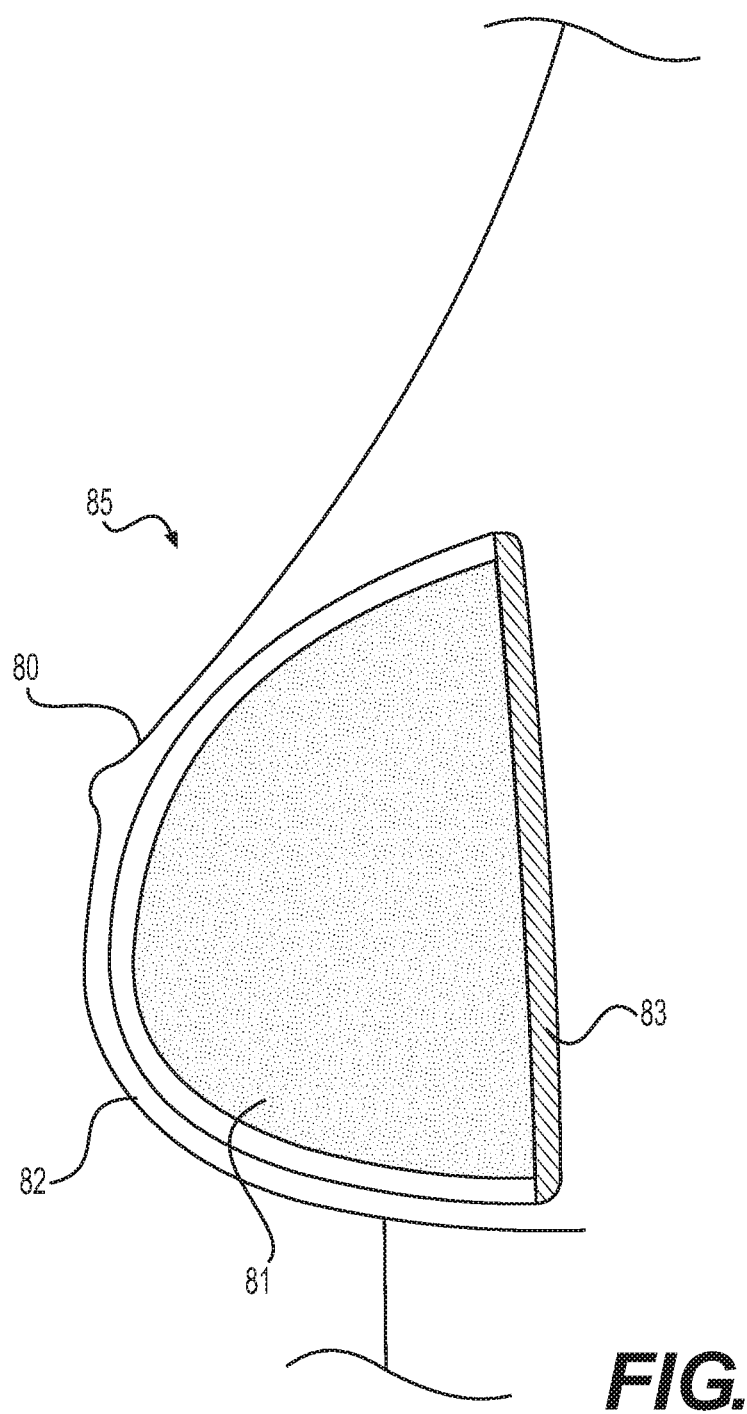
FIG. 8 illustrates the tissue product of FIG. 7 implanted within a breast to facilitate a breast augmentation, reconstruction, or other breast procedure.

FIG. 7 is a side view of another tissue product 80, for use as a breast implant, and FIG. 8 illustrates implantation of the device 80 within a breast 85. As shown, the device 80 includes including two sheets 82, 83 of acellular tissue matrix and a porous tissue matrix sponge 81 secured between the sheets to form a volume shaped for implantation within a breast.

The device 80 is illustrated having the shape of a typical breast implant, such as a rounded or teardrop implant. The devices 80, however, of the present disclosure need not have typical breast implant (teardrop or rounded) shapes. For example, the devices can have other shapes including, for example, irregular shapes, spherical shapes, ovoid shapes, or custom-made shapes based on patient anatomy or treatment site. For example, a surgeon may select a spherical or custom-made shape for implantation in a lumpectomy site or based on patient-specific factors. In addition, the surgeon may select two- or more implants to be implanted next to one another or in different locations. In addition, although described in particular with respect to breast implants the presenting disclosed implants, systems, and methods can be used at other sites where synthetic implants may be used (e.g., gluteal implants).

As discussed above, the two sheets 82, 83 can include intact acellular tissue matrix, but can be formed from tissue matrix derived from different tissue types. For example, in one embodiment, the first sheet 82, which may form an anterior or frontal portion of the implant 80 can be formed from a tissue matrix selected to allow cellular ingrowth and tissue regeneration, while also providing sufficient mechanical properties (e.g., tensile strength, burst strength, suture retention strength) to allow the sheet 82 to provide structural support and load-bearing capacity, as may be needed to support a mass of the tissue matrix sponge 81 and surrounding breast structures. In some embodiments, the sheet 82 is a dermal acellular tissue matrix such as ALLODERM® or STRATTICE™. The sheet can include other tissue such as bladder, intestinal layer(s), stomach layer(s), dura, pericardium, skeletal muscle, nerve, peritoneum, or fascia.

The second sheet 83 can be produced from a different tissue. For example, one suitable tissue can include a muscle tissue matrix. Suitable muscle matrix materials are described in US Patent Publication Number 2015/0282925A1 (application Ser. No. 14/410,204), which was filed on Jul. 1, 2013 to Xu et al.

As shown in FIG. 8, the device 80 can be implanted within the breast 85 with the first sheet 82 facing substantially anteriorly, and the second sheet 83 facing posteriorly and near or in contact with chest wall muscles (e.g., the pectoralis muscles). As such, the first sheet 82 can be configured to allow cellular ingrowth and tissue revascularization from cutaneous or immediately subcutaneous tissues, or from anteriorly located tissue within a pocket formed in a breast 90. In addition, the second sheet 83 can allow cellular ingrowth from posteriorly located (relative to the implant 80) tissues such as muscle, and may support desired muscle generation.

As discussed above, the devices described herein in each of the figures can include acellular tissue matrix sponge (11, 21, 31, 41, 51, 61, 71, 81). As used herein, tissue matrix sponge will be understood to refer to a tissue matrix material that has been processed to produce a sponge-like matrix. The sponge-like matrix can be formed of an extracellular tissue matrix (ECM) that retains ECM components including extracellular collagen, glycoproteins, and other molecules important for supporting cellular ingrowth and tissue regeneration.

As used herein, the term "tissue matrix sponge" will be understood to refer to a tissue matrix material that includes extracellular tissue matrix (ECM) (including collagen and important non-collagenous proteins), wherein the ECM has been mechanically processed to form fragments or particles, and has been resuspended or reformed (e.g., by casting and drying) to form a porous sponge-like material. The sponge properties can be tailored by selecting an appropriate tissue type (e.g., using adipose, dermis, muscle, fascia, nerve, vascular tissue, intestinal components, skeletal muscle, peritoneum, tendon, ligament, or other appropriate tissue).

Further, the tissue properties can be modified by controlling solid content of the sponge (i.e., the about of tissue matrix present in suspension). Higher solid content will generally form higher modulus and stronger materials. Additional modifications to the material to adjust mechanical properties can include chemical cross linking, particle or fiber sizes, increasing solid content per volume through compression, and pattern molding with fiber alignment for directional properties.

The tissue matrix sponge can be formed from a number of tissue matrix types and with a number of processes. For example, in some embodiments, the tissue matrix sponge is formed from adipose tissue. Suitable adipose tissues are described generally is number US Patent Publication Number 2012/0310367A1 (U.S. application Ser. No. 13/483,674, filed May 30, 2012, to Connor). Such adipose materials can be formed generally by mechanical homogenization, washing, resuspension, and stabilization of the material. The material may be dried (e.g. by freeze drying before or after stabilization), and stabilization can be by dehydrothermal treatment (DHT), cross-linking (UV, radiation, or chemical cross-linking). The stabilization can further be used to bond or attach the sponge to the other material. For example, DHT treatment can cause some degree of cross-linking, which can be improved by surface roughening to texturing (see e.g., FIG. 3, item 53). In addition, the sponge may be sterilized before or after joining to the intact tissue matrix. Sterilization may be performed after the components of the devices described herein are joined. Further, the sponge may be formed while in contact with the intact acellular tissue matrix components, or may be formed separately prior to joining.

In addition, although the devices shown above have a number of layers or components, it will be appreciate that the structures can include additional layers. For example, devices including multiple layers of the components shown in the figures may be used. And multiple layers of the tissue matrix components can be added, for example, to improve device strength.

As noted above, the products discussed herein can be used for treatment of breast. And, in varying embodiments, the intact acellular tissue matrix component and porous tissue matrix sponge can be provided either as a single premanufactured article, or as separate components to be implanted by a surgeon, or as combinations of single articles and separate components (e.g., for different section of a treatment site).

Figure 10:
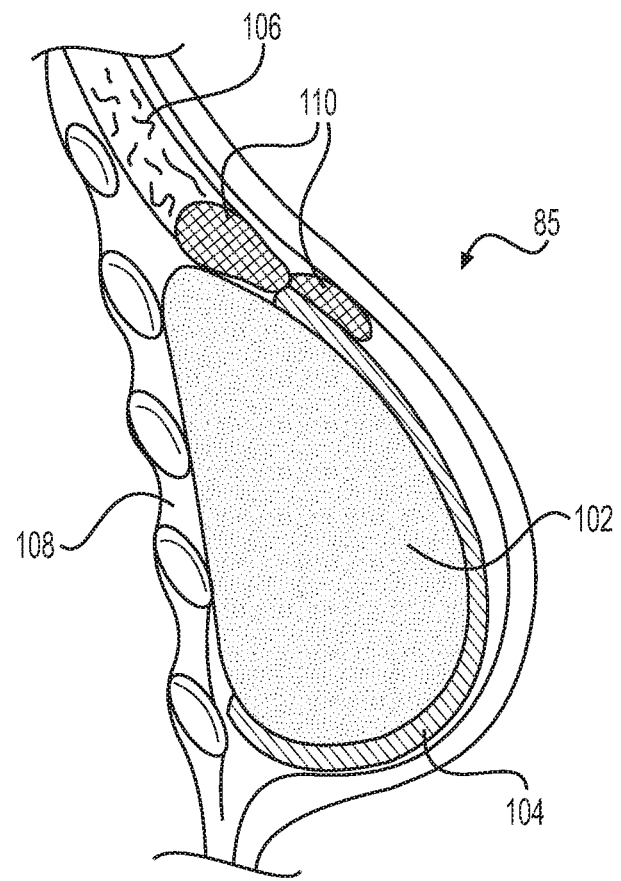
FIG. 10 illustrates a side cut away view of tissue products within a breast to facilitate an improved breast procedure using products and methods of the present disclosure.

For example, FIG. 10 illustrates a side cut away view of a prospective use of the tissue product of FIG. 7 implanted, together with additional tissue products, within a breast to facilitate an improved breast procedure using products and methods of the present disclosure.

As shown, the products of the present disclosure can be implanted at a breast 85 treatment site, e.g., for augmentation or reconstructive procedures. As such, the products can be used in conjunction with various implants 102 or similar devices (e.g., tissue expanders) and can be used for a variety of implant procedures and location (e.g., subcutaneous or subpectoral). And the products of the present disclosure, including an intact acellular tissue matrix sheet 104 can be implanted to support the implant or tissue expander and/or to facilitate other goals (e.g., provide tissue coverage, restore blood flow, etc.).

In some breast treatment procedures, however, in addition to the benefits provided by the intact tissue matrix sheets, it is desirable to implant other tissue, such as adipose tissue matrix sponge, to provide additional implant coverage. For example, in some cases, e.g., with thin patients, the implant may cause undesirable effects such as skin rippling or less than desirable shapes (e.g., due to the bulk of the implant at the superior portion or other areas with insufficient breast tissue coverage).

Accordingly, in various embodiments, a surgeon may use a sheet of tissue matrix 104 and a tissue matrix sponge such as adipose matrix 110. The adipose matrix can be provided as a separate component and implanted where needed, or can be provided preassembled and attached to the sheet of tissue matrix (as shown in FIG. 11). In the latter case, the sponge 134 can be provided with sufficient bulk so that the surgeon can shape or contour (e.g., remove portions) of the sponge to produce a desired implant.

The sponge 110 or 134 can be implanted at a variety of sites around the breast to prevent rippling, reduce undesired shapes (e.g., reduce appearance of the superior portion of the implant as illustrated in FIG. 10), and/or to improve overall aesthetic results.

The above description and embodiments are exemplary only and should not be construed as limiting the intent and scope of the invention.

What is claimed is:

1. A tissue product, comprising:
    a first component comprising an intact acellular dermal tissue matrix; and
    a second component comprising a porous acellular adipose tissue matrix sponge covering at least a portion of the intact acellular tissue matrix, wherein the porous acellular tissue matrix sponge comprises a tissue matrix that has been mechanically homogenized, resuspended, and stabilized, and wherein the intact acellular tissue matrix and porous acellular tissue matrix sponge are attached such that the intact acellular tissue matrix provides mechanical support to the porous acellular tissue matrix sponge.

2. The tissue product of claim 1, wherein the intact acellular tissue matrix is in the form of a sheet.

3. The tissue product of claim 2, wherein the porous acellular tissue matrix sponge covers at least one side of the sheet.

4. The tissue product of claim 2, wherein at least a portion of a surface of the intact acellular tissue matrix is textured, roughened, or indented.

5. The tissue product of claim 1, further comprising at least one additional acellular tissue matrix, comprising a skeletal muscle matrix.

6. The tissue product of claim 1, wherein the first component comprising the intact acellular tissue matrix comprises a group of openings.

7. The tissue product of claim 6, wherein the intact acellular tissue matrix is in the form of a sheet, and the group of openings comprises a group of holes passing through the sheet.

8. A tissue product, comprising:
    a first component comprising a sheet of acellular dermal tissue matrix; and
    a second component comprising a porous acellular tissue matrix sponge covering at least a portion of the intact acellular tissue matrix, wherein the second component consists essentially of adipose tissue matrix.

9. The tissue product of claim 8, wherein the porous acellular tissue matrix sponge covers at least one side of the sheet.

10. The tissue product of claim 8, wherein the porous acellular tissue matrix sponge covers a top side and a bottom side of the sheet.

11. The tissue product of claim 8, wherein at least a portion of a surface of the sheet of acellular tissue matrix is textured, roughened, or indented.

12. The tissue product of claim 8, further comprising at least one additional acellular tissue matrix sheet, comprising a skeletal muscle matrix.

13. The tissue product of claim 8, wherein the first component comprising a sheet of acellular tissue matrix comprises a group of openings.

14. A tissue product, comprising:
a first component comprising a sheet of acellular tissue matrix;
a second component comprising a sheet of a second acellular tissue matrix derived from a tissue type different than that of the first component; and
a third component comprising a porous acellular tissue matrix sponge, wherein the third component is contained between the first component and the second component.

15. The tissue product of claim 14, wherein the first component comprises a sheet of acellular dermal tissue matrix.

16. The tissue product of claim 14, wherein the second component comprises at least one of a sheet of acellular skeletal muscle tissue matrix or a sheet of acellular dermal tissue matrix.

17. The tissue product of claim 14, wherein the first component and second component form a cavity, and the third component is located within the cavity.

18. The tissue product of claim 17, wherein the third component is completely surrounded by the first component and the second component.

19. The tissue product of claim 14, wherein the third component comprises adipose tissue matrix.

20. The tissue produce of claim 14, wherein the tissue product is in the shape of a breast implant.

21. The tissue product of claim 20, wherein the first component has a convex shape forming an anterior surface of the breast implant.

22. The tissue product of claim 20, wherein the first component is a dermal tissue matrix sheet, and the second component is a skeletal muscle tissue matrix sheet.

23. The tissue product of claim 22, wherein the first component and second component completely enclose the third component.

24. The tissue product of claim 14, wherein at least one of the first component and the second component comprises a group of openings passing through the sheet.

* * * * *